(12) United States Patent
Spreiter et al.

(10) Patent No.: US 12,708,413 B2
(45) Date of Patent: Aug. 18, 2026

(54) BONE PLATE AND GUIDE BLOCK COUPLING MECHANISM

(71) Applicant: DePuy Synthes Products, Inc., Raynham, MA (US)

(72) Inventors: Gregor Spreiter, Basel (CH); Alexander Ludin, Berne (CH); Marcel Schweizer, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 250 days.

(21) Appl. No.: 18/537,586

(22) Filed: Dec. 12, 2023

(65) Prior Publication Data

US 2025/0186094 A1 Jun. 12, 2025

(51) Int. Cl.
*A61B 17/80* (2006.01)
*A61B 17/00* (2006.01)

(52) U.S. Cl.
CPC .... *A61B 17/80* (2013.01); *A61B 2017/00477* (2013.01)

(58) Field of Classification Search
CPC ...................... A61B 17/80; A61B 2017/00477
See application file for complete search history.

(56) References Cited

U.S. PATENT DOCUMENTS 8,491,593 B2 7/2013 Prien et al.
8,968,371 B2 3/2015 Humphrey
10,731,687 B2 8/2020 Ponzer et al.
11,065,042 B2 7/2021 Garvey et al.
11,076,898 B2 8/2021 Langdale et al.
11,331,128 B2 * 5/2022 Zingalis ............. A61B 17/1728
11,644,053 B2 * 5/2023 Lindenmann ............. F16B 7/18 403/343
2017/0049493 A1 2/2017 Gauneau et al.
2022/0240991 A1 8/2022 Zingalis et al.

FOREIGN PATENT DOCUMENTS

CN 106061412 A 10/2016
CN 110177512 A 8/2019
EP 4169461 A1 4/2023

OTHER PUBLICATIONS

International Search Report and Written Opinion dated Apr. 2, 2025, from corresponding International Application No. PCT/IB2024/061795.

* cited by examiner

*Primary Examiner* — Si Ming Ku

(57) ABSTRACT

A bone plate comprises three receiving components. A guide block comprises three coupling components. The first receiving component and the first coupling component mate with one another such that relative motion between the first receiving component and the first coupling component is restricted in a first degree of freedom, a second degree of freedom, and a third degree of freedom. The second receiving component and the second coupling component mate with one another such that relative motion between the second receiving component and the second coupling component is restricted in a fourth degree of freedom and a fifth degree of freedom. The third receiving component and the third coupling component mate with one another such that relative motion between the third receiving component and the third coupling component is restricted in a sixth degree of freedom.

20 Claims, 12 Drawing Sheets

62
60
66
64
68
204
300
100
200
304
302

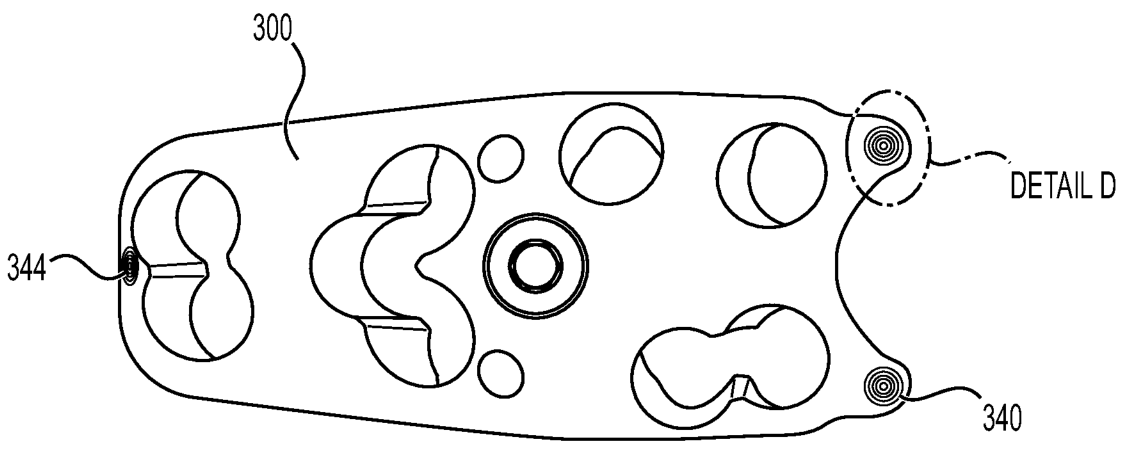
FIG. 9A
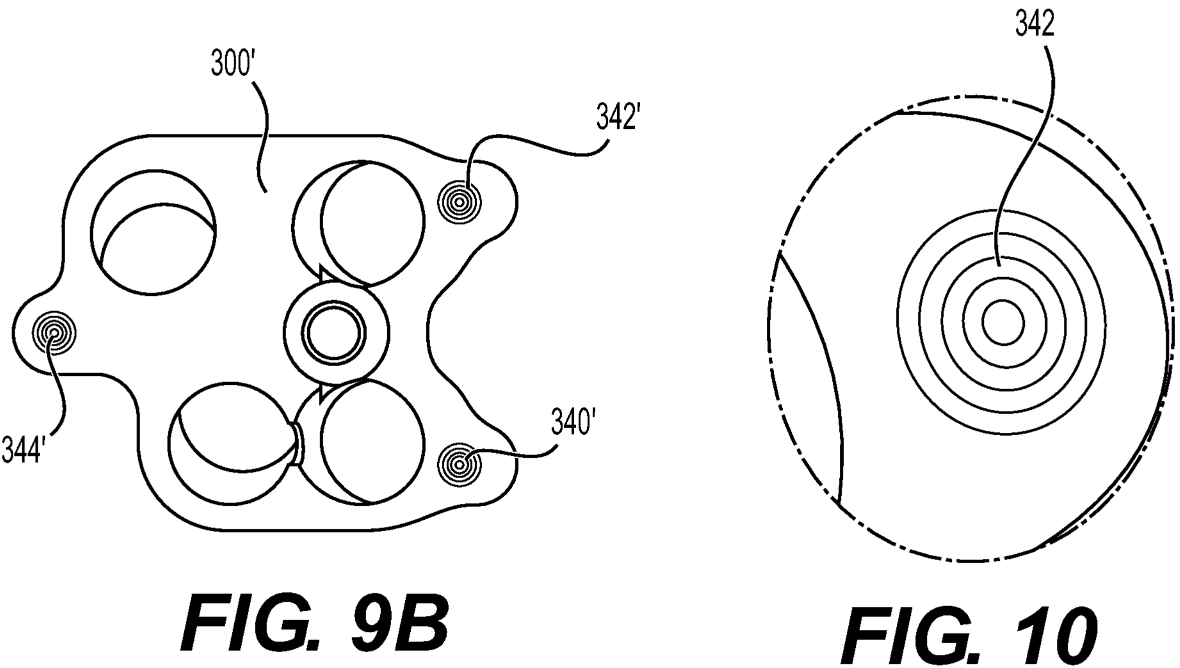
FIG. 9B
FIG. 10

BONE PLATE AND GUIDE BLOCK COUPLING MECHANISM

FIELD

The present invention generally relates devices and methods for mating a guide block to a bone plate. More specifically, the present invention relates to mating a guide block to a bone plate with greater accuracy.

BACKGROUND

Guide blocks are used with a bone plate to treat fractures in bones in the body. Guide blocks have multiple purposes. Guide blocks are used with a bone plate to ensure accurate placement of drill holes relative to the plate holes. Guide blocks also protect soft tissues of the patient from a rotating drill. Guide blocks also prevent the drill from scratching the bone plate. Scratches can act as stress raisers and may result in plate fatigue failure due to a concentrated load.

The position of the guide block with respect to the bone plate is determined by the actual shape of the under-surface of the guide block and the top surface of the bone plate. Because every surface has a tolerance of form, large differences may occur where the contact points between a guide block and a bone plate are and where the guide block holes relative to the plate holes are located. Thus, the position of the guide block with respect to the bone plate is based on one of three mating spheres, but it is not possible to know which of the three mating points determines the relative position of the bone plate with respect to the guide block. To be able to know the position of the bone plate with respect to the guide block would require very tight tolerances for the contact features to keep sufficient alignment between guide block holes and plate holes, which is very expensive and may not even be possible to produce and inspect. Moreover, to verify the design, multiple tolerance analyses would be required to check each of the three scenarios of all three spherical contact points as a definition of the relative position. Thus, there is a need in the art for a guide block and bone plate construction that will permit greater accuracy in determining the position of the bone plate with respect to the guide block.

SUMMARY

The presently disclosed technology achieves greater accuracy in determining the position of the bone plate with respect to the guide block by modifying the structure of the mating surfaces of the guide block and the bone plate.

In some examples, the present disclosure includes a bone plate and guide block system that includes a bone plate comprising a first receiving component, a second receiving component, and a third receiving component. A guide block comprises a first coupling component, a second coupling component, and a third coupling component. The first receiving component and the first coupling component being adapted to mate with one another such that relative motion between the first receiving component and the first coupling component is restricted in a first degree of freedom, a second degree of freedom, and a third degree of freedom. The second receiving component and the second coupling component being adapted to mate with one another such that relative motion between the second receiving component and the second coupling component is restricted in a fourth degree of freedom and a fifth degree of freedom. The fourth and fifth degrees of freedom being non-overlapping with the first, second, and third degrees of freedom. The third receiving component and the third coupling component being adapted to mate with one another such that relative motion between the third receiving component and the third coupling component is restricted in a sixth degree of freedom. The sixth degree of freedom being non-overlapping with the first, second, third, fourth and fifth degrees of freedom.

Other aspects and features of the present disclosure will become apparent to those skilled in the pertinent art, upon reviewing the following detailed description in conjunction with the accompanying figures.

BRIEF DESCRIPTION OF THE DRAWINGS

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 9A is a top plan view of the guide block showing concentric circles on the first, second and third coupling components of the guide block.

FIG. 9B is a top plan view of the shortened guide block showing concentric circles on the first, second and third coupling components of the shortened guide block.

FIG. 10 is an enlarged view of the second coupling component of FIG. 9A.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 80%" may refer to the range of values from 61% to 99%.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Figure 1:
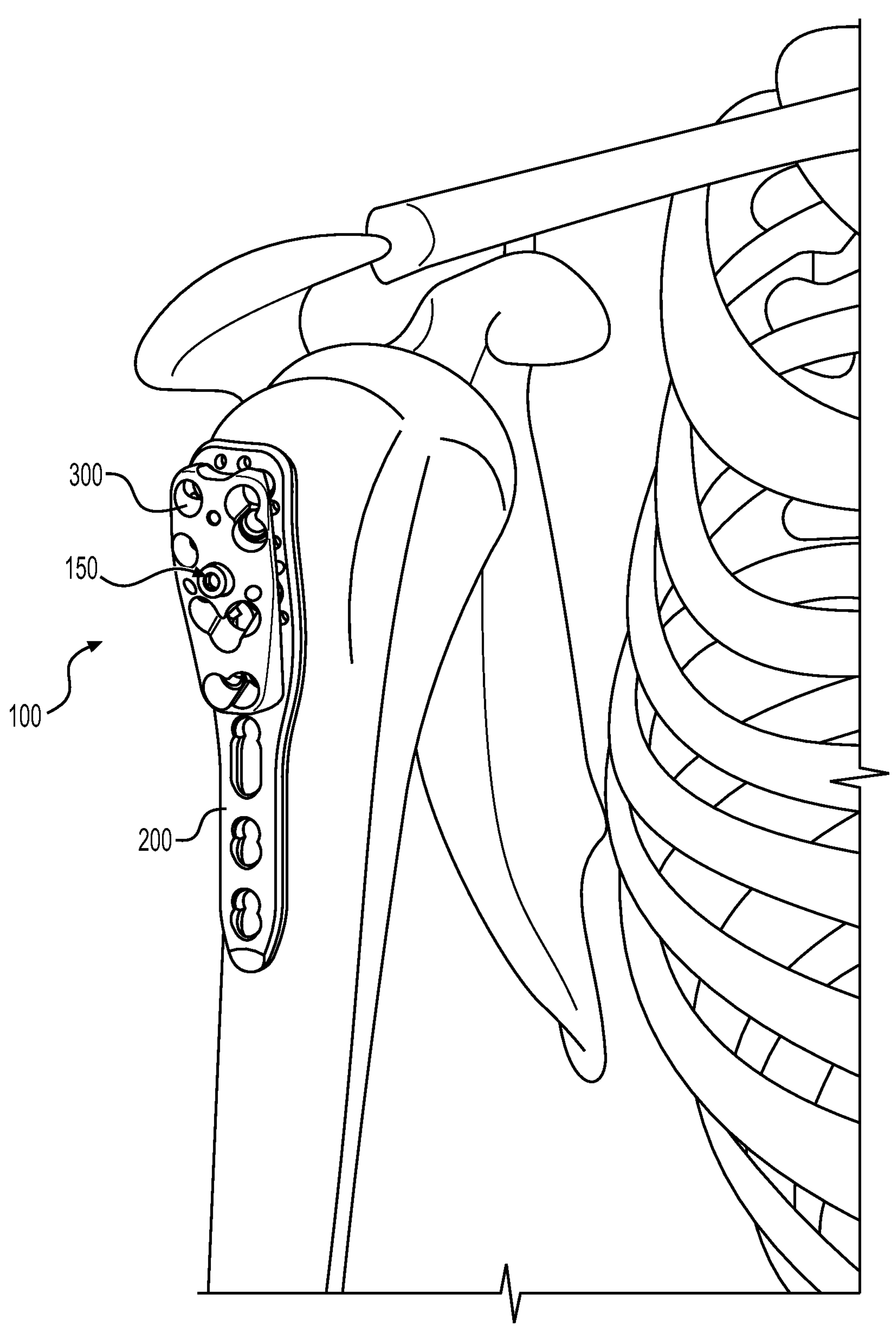
FIG. 1 is a perspective view of a bone plate and guide block on a humerus bone in accordance with the present disclosure.

Referring now to FIG. 1, a guide block system 100 is illustrated. Guide block system 100 is shown on a humerus bone of a patient for treating a fracture in the humerus bone. Of course, the guide block system 100 in accordance with the present disclosure can be used to treat bone fractures on just about any bone in the body. Guide block system 100 includes a bone plate 200 and a guide block 300 that are mated together and used together to treat a bone fracture.

Figures 2A, 2B, 2C:
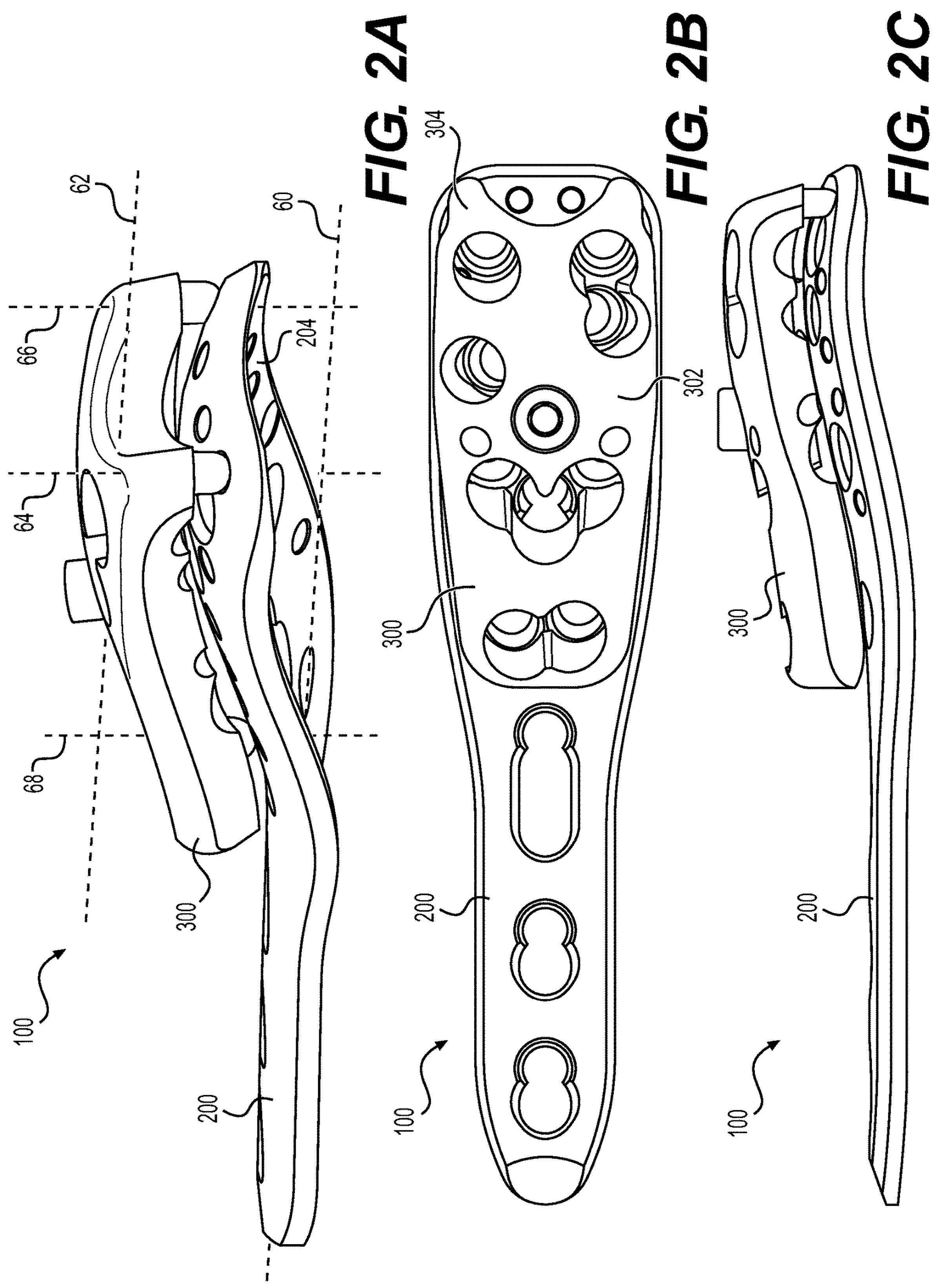
FIG. 2A is a perspective view of a bone plate and a guide block mated together.
FIG. 2B is a top view of a bone plate and a guide block mated together.
FIG. 2C is a side view of a bone plate and a guide block mated together.

Referring now to FIGS. 2A-2C, guide block 300 is shown mated to bone plate 200. Guide block 300 has three points of contact with bone plate 200 along a first axis 64, a second axis 66, and a third axis 68, respectively. The first axis 64, the second axis 66, and the third axis 68 are generally orthogonal to a first longitudinal axis 60 of the bone plate 200. The first axis 64, the second axis 66, and the third axis 68 are also generally orthogonal to a second longitudinal axis 62 of the guide block 300.

Figure 4A:
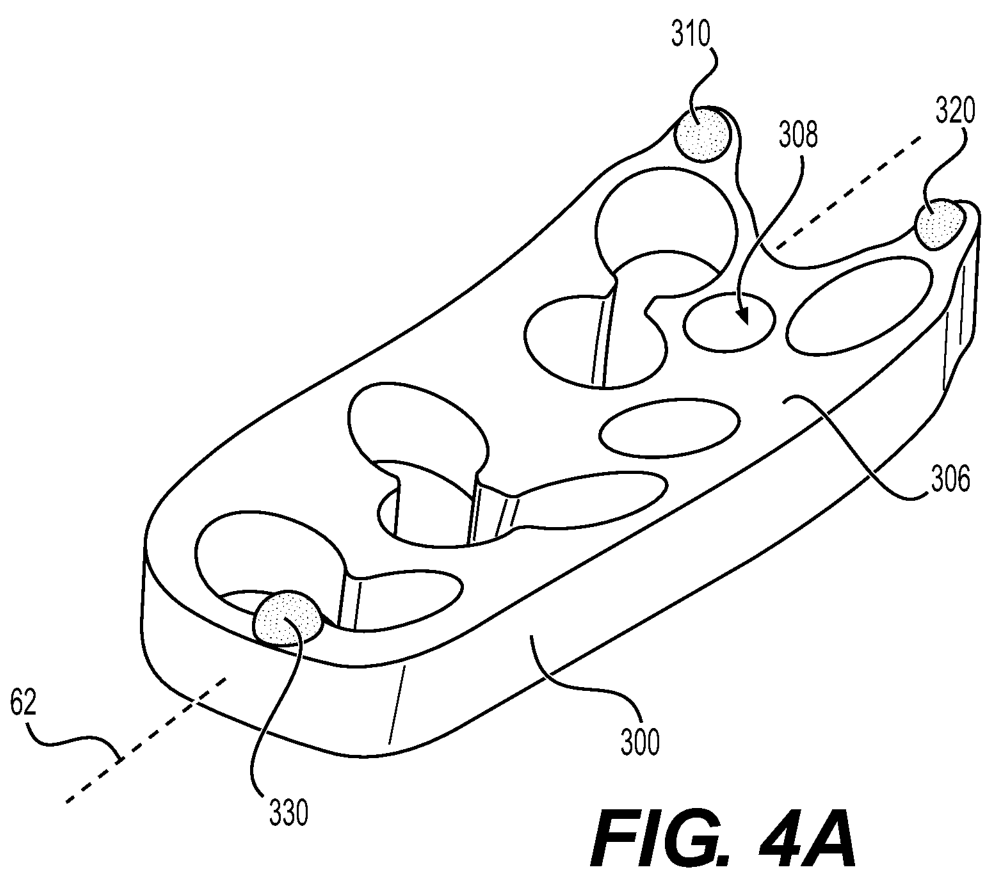
FIG. 4A is a perspective view of a standard size guide block.
Figure 4B:
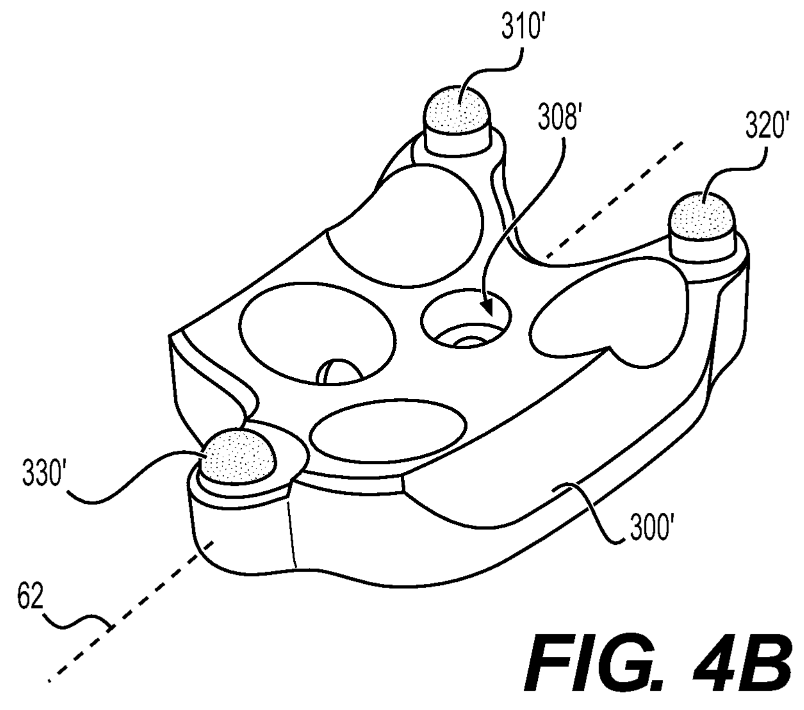
FIG. 4B is a perspective view of a shortened guide block.

A standard size guide block 300 is shown in FIG. 4A. Guide block 300 has a longitudinal axis 62, a lower surface 306 and three coupling components 310, 320, 330. In the example shown, each coupling component is a hemispherical-shaped projection that projects away from surface 306. Alternatively, one or more of the coupling components could have a cone shape. A longitudinally shorter guide block 300' is shown in FIG. 4B. Guide block 300' has a longitudinal axis 62', a lower surface 306' and three coupling components 310', 320', 330'. In the example shown, each coupling component is a hemispherical-shaped projection that projects away from surface 306'. Guide block 300 extends along longitudinal axis 62.

Figure 3:
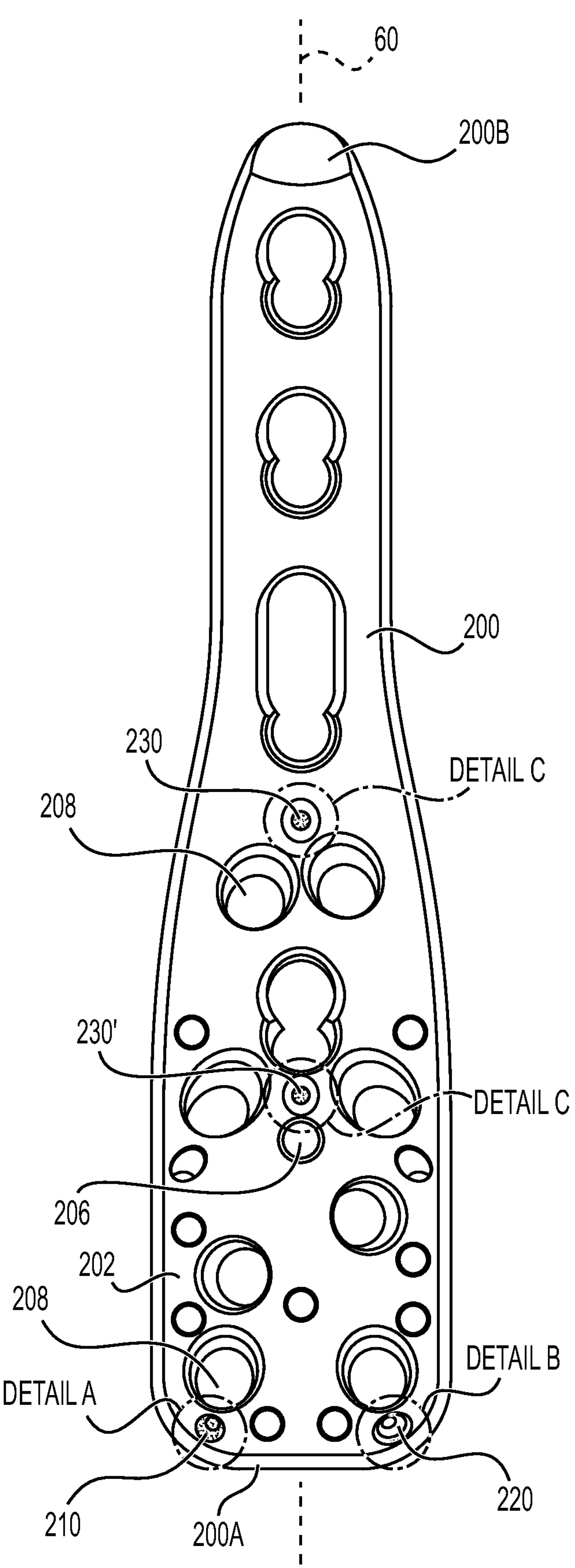
FIG. 3 is a top view of a bone plate.
Figure 5A:
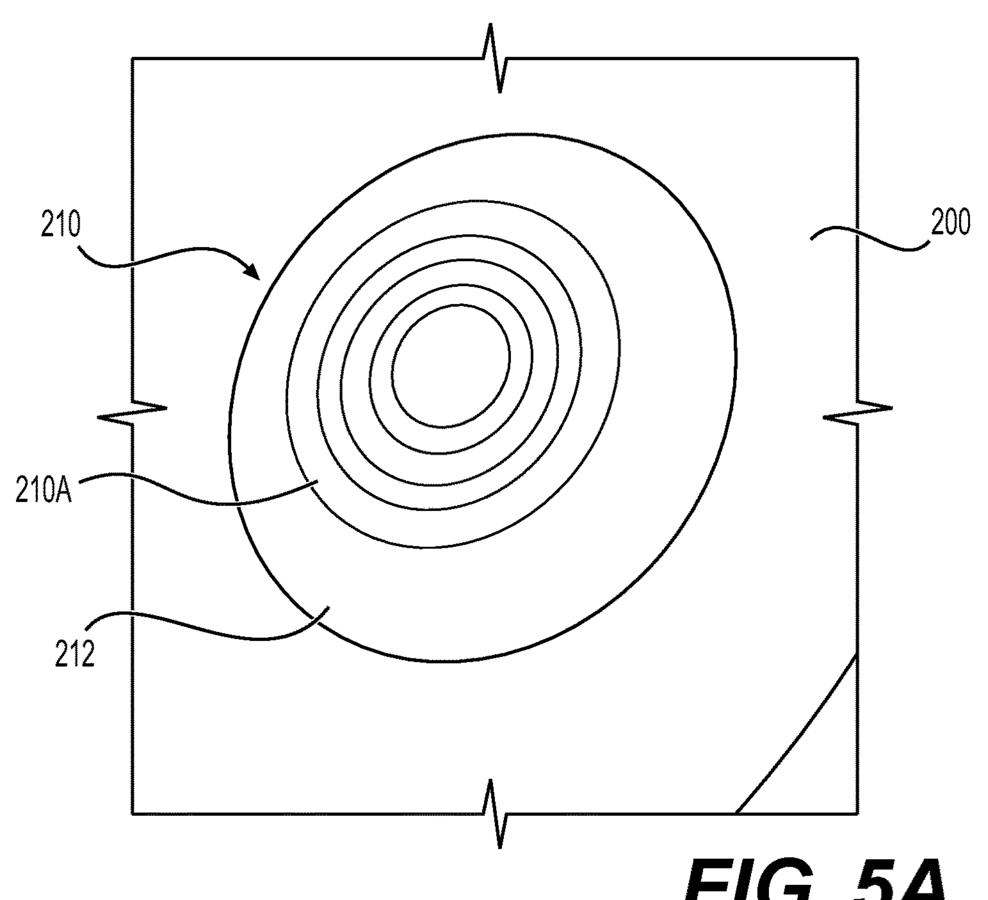
FIG. 5A is an enlarged view of a first receiving component of the bone plate.

A bone plate 200 is shown in FIG. 3. As mentioned above, bone plate 200 has a longitudinal axis 60. Bone plate 200 also has a first lateral end 200A, a second lateral end 200B, an upper surface 202, a lower surface 204, at least one post bore 206 and a plurality of plate bores 208 defined through the body of bone plate 200. Bone plate 200 has a first receiving component 210, a second receiving component 220, and a third receiving component 230 as shown in FIG. 3. More specifically and referring now to FIGS. 5A-5C, bone plate 200 has a first recess 210A formed in the upper surface 202 and defining a first semi-spherical or hemispherical surface 212. A second recess 220A is formed in the upper surface 202 and defines opposing parallel ledges 222 proximal an upper end of the second recess 220A. The second recess 220A can be elongated in a length direction of the second recess 220A relative to a width direction of the second recess 220A. A third recess 230A is formed in the upper surface 202 and defines a planar bottom surface 232.

As discussed above, guide block 300 has a first coupling component 310, a second coupling component 320, and a third coupling component 330. Guide block 300' has a first coupling component 310', a second coupling component 320', and a third coupling component 330'. The coupling components 310, 320, 330, 310', 320', 330' each have a hemispherical shaped projection that projects away from a lower surface 306, 306' of the respective guide block 300, 300'.

Referring now to FIGS. 2A-2C, 5A and 6, the first receiving component 210 and the first coupling component 310 mate with one another. First coupling component 310 has a hemispherical shaped projection. First receiving component 210 has a hemispherical shaped recess 210A that is shaped to receive the hemispherical shape of the first coupling component 310 such that, when mated, relative motion between the first receiving component 210 and the first coupling component 310 is restricted in a first degree of freedom, a second degree of freedom, and a third degree of freedom. The first degree of freedom is movement along the x-axis. The second degree of freedom is movement along the y-axis. The third degree of freedom is movement along the z-axis. The fourth, fifth and sixth degrees of freedom are sometimes referred to as roll, pitch, and yaw. Roll is rotation about the x-axis, pitch is rotation about the y-axis and yaw is rotation about the z-axis.

Figure 5B:
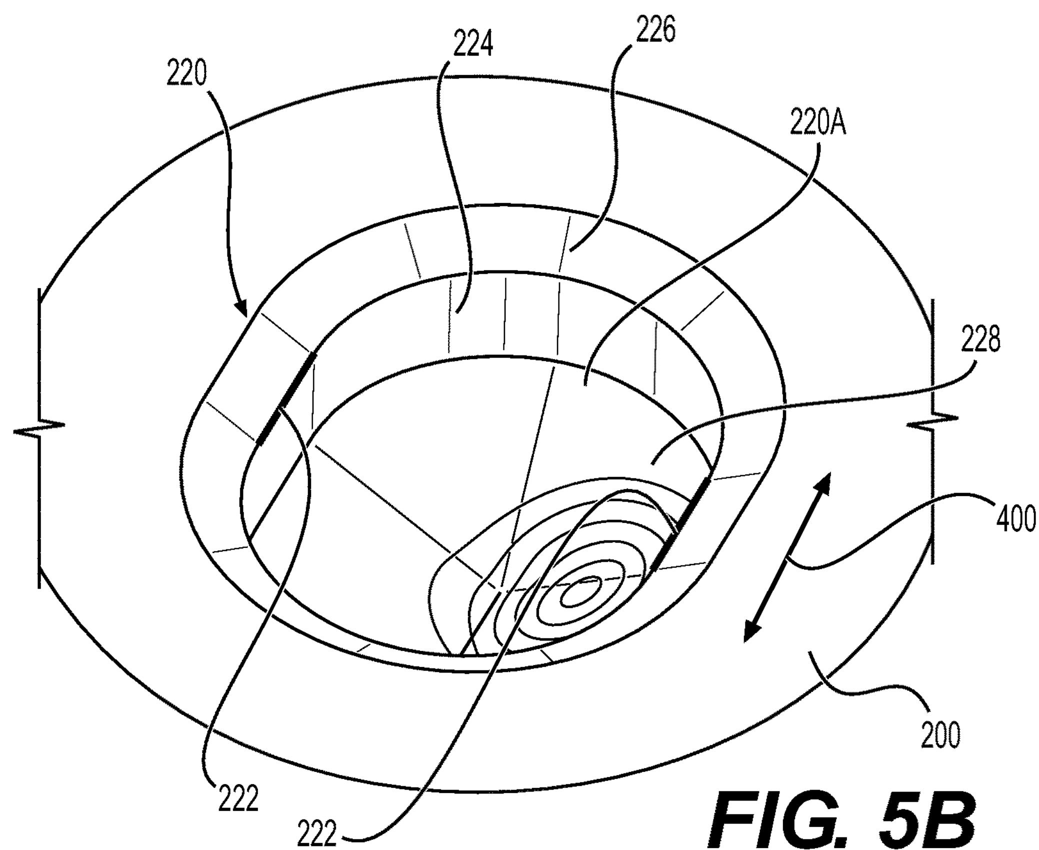
FIG. 5B is an enlarged view of a second receiving component of the bone plate.
Figure 5C:
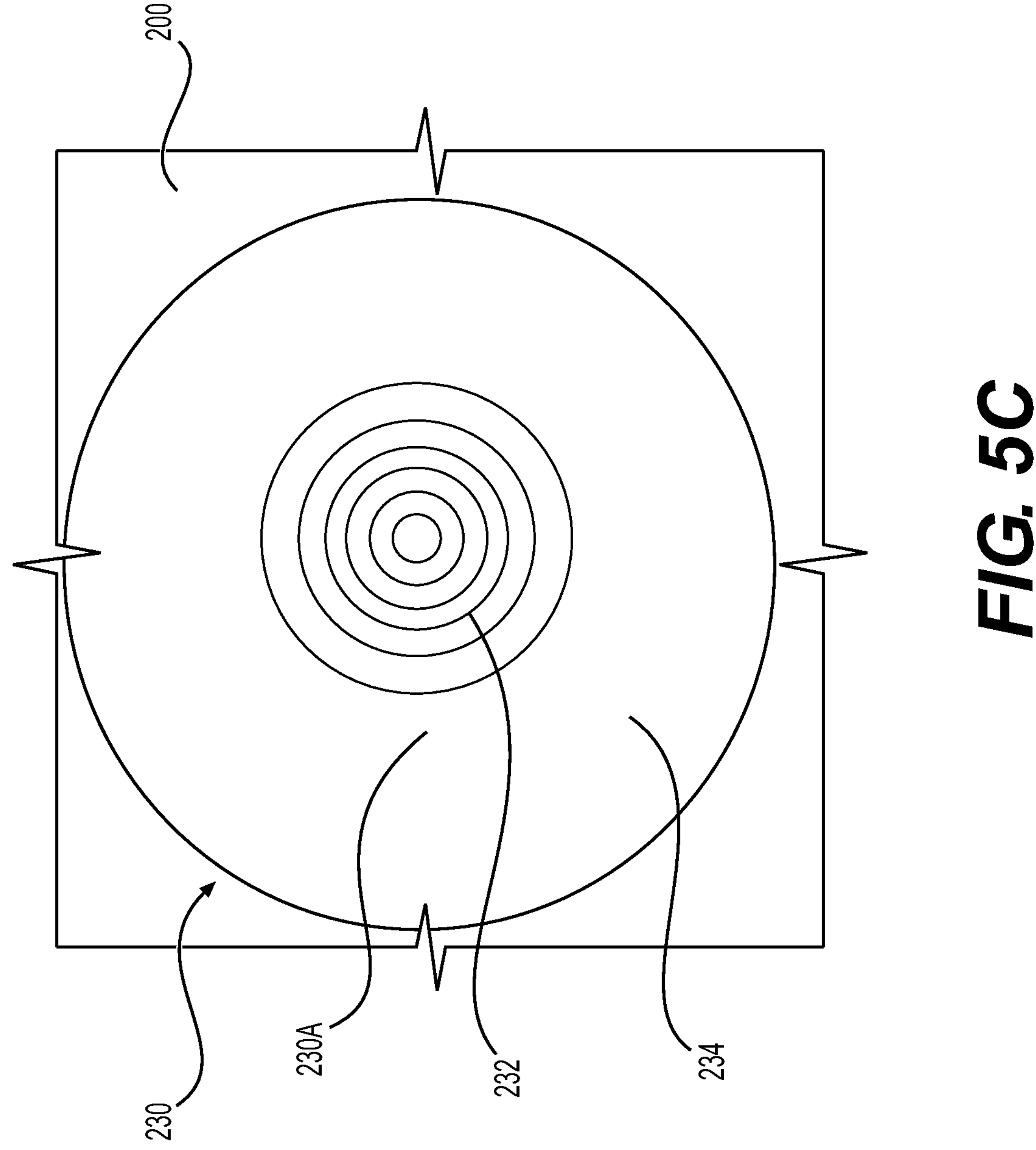
FIG. 5C is an enlarged view of a third receiving component of the bone plate.
Figure 6:
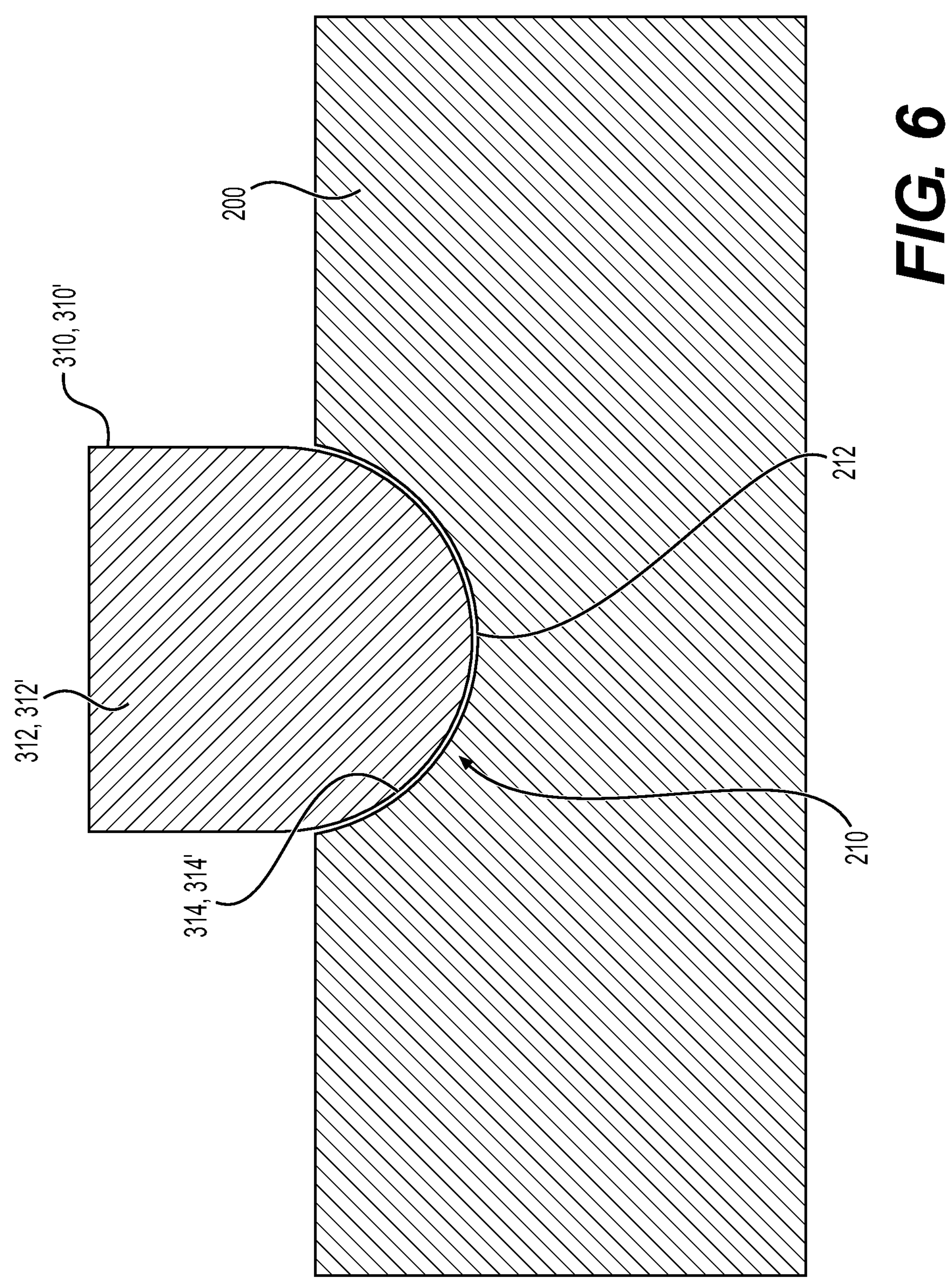
FIG. 6 is a side cross-sectional view of the first receiving component of the bone plate mating with a first coupling component of the guide block.
Figure 7A:
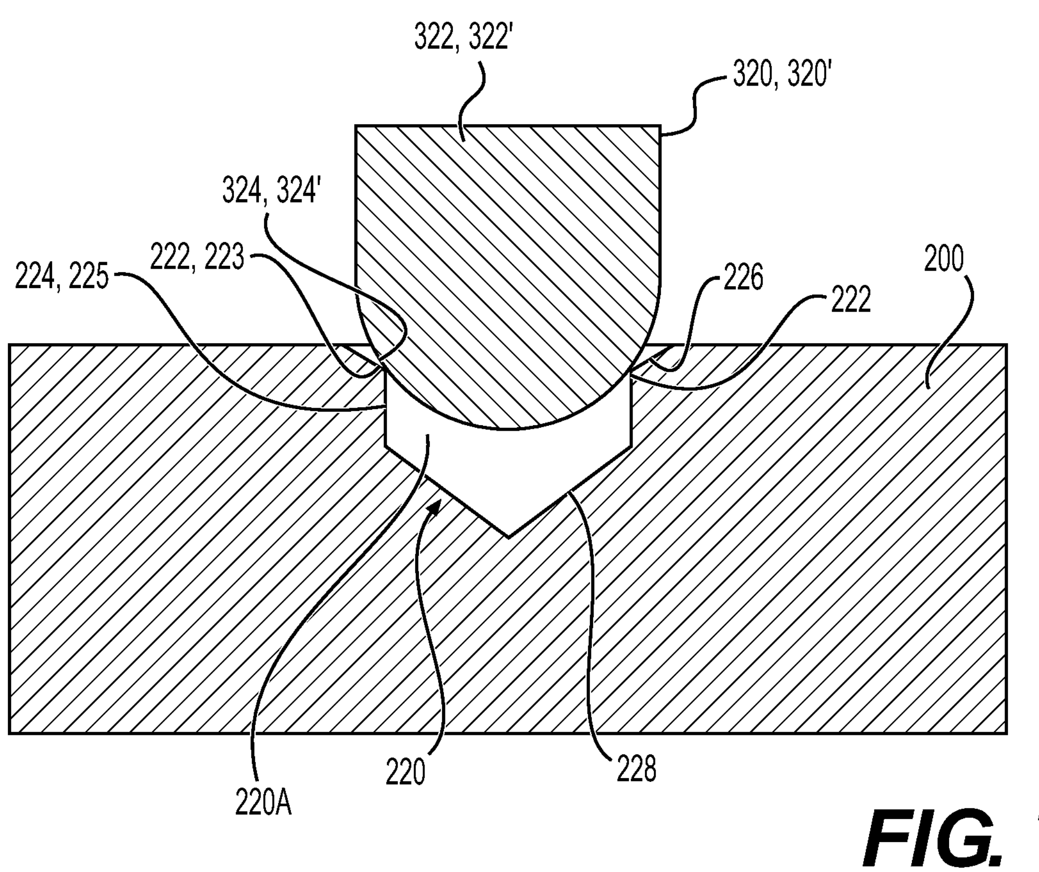
FIG. 7A is a side cross-sectional view of the second receiving component of the bone plate mating with a first coupling component of the guide block.
Figure 7B:
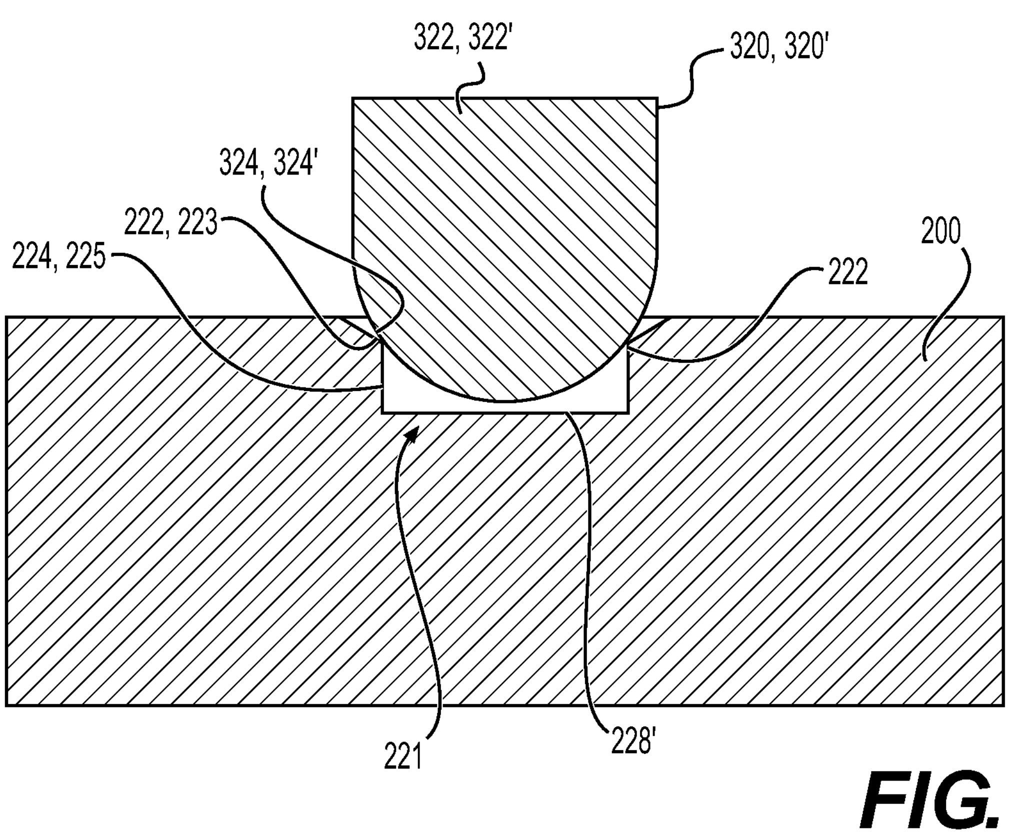
FIG. 7B is a side cross-sectional view of another embodiment of the second receiving component of the bone plate mating with a second coupling component of the guide block.
Figure 7C:
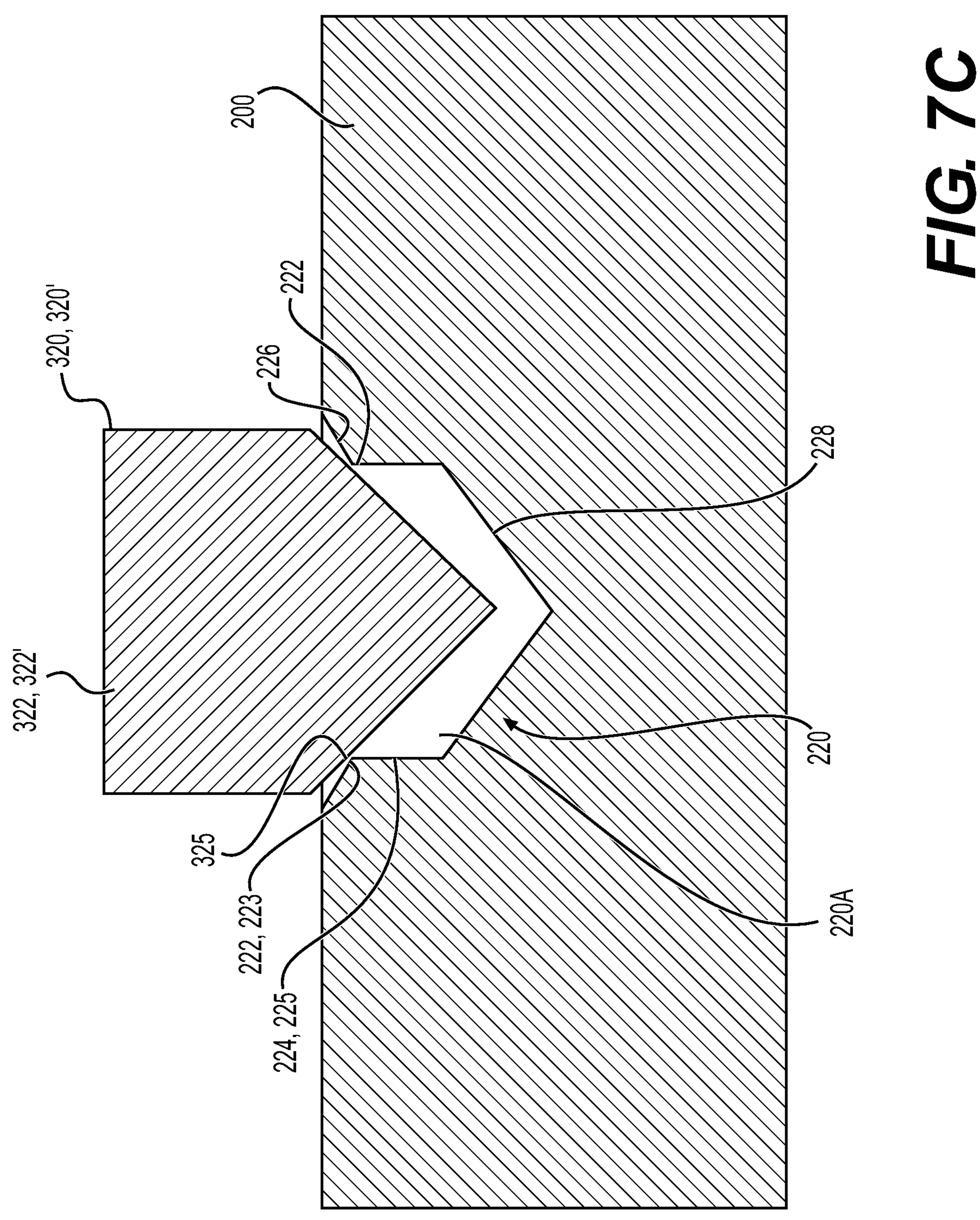
FIG. 7C is a side cross-sectional view of another embodiment of the second receiving component of the bone plate mating with a second coupling component of the guide block.

Referring now to FIGS. 2A-2C, 5B, and 7A-7C, the second receiving component 220 and the second coupling component 320 mate with one another. Second coupling component 320 has a hemispherical shaped projection. Second coupling component 320, 320' can, alternatively, have a conical (e.g., cone, frustoconical, etc.) shape projection. Second receiving component 220 has a second recess 220A that is shaped to receive the hemispherical shape of the second coupling component 320 such that, when mated, relative motion between the second receiving component 220 and the second coupling component 320 is restricted in a fourth degree of freedom and a fifth degree of freedom. The fourth and fifth degrees of freedom are non-overlapping with the first, second, and third degrees of freedom. As shown in FIG. 5B, second recess 220A is in the shape of an elongated oval with opposing parallel ledges 222. Opposing ledges 222 are defined by an upper edge of a sidewall 224 of the second recess 220A and a lower edge of a chamfer 226 such that the opposing ledges 222 are disposed below the upper surface 202 of the rigid plate body. As shown in FIGS. 7A-7C, the bottom surface 228, 228' of second recess 220, 220' is spaced from the bottom surface of the second coupling component 320, 320', respectively. Thus, second coupling component 320, 320' contacts ledge 222 at two locations. More specifically, second coupling component 320, 320' contacts ledge 222 at one point of contact on each ledge as shown in FIGS. 7A-7C. In other examples, the second recess 220 can be formed such that the sidewall takes a cylindrical shape 225 with a cylindrical upper ledge 223, rather than the shape of an elongated oval. In this example, the second coupling component 320, 320' contacts the cylindrical ledge 223.

Figure 8A:
FIG. 8A is a side cross-sectional view of the third receiving component of the bone plate mating with a third coupling component of the guide block.
Figure 8A:
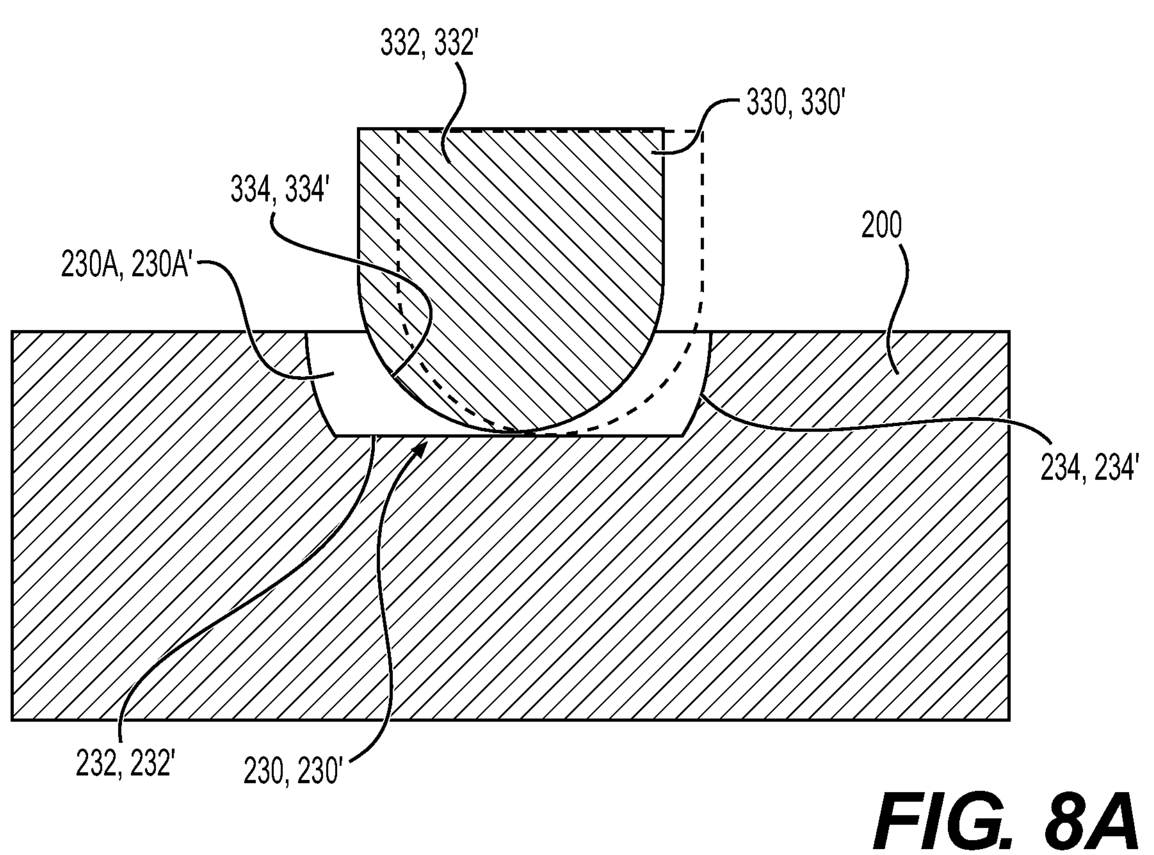
Figure 8B:
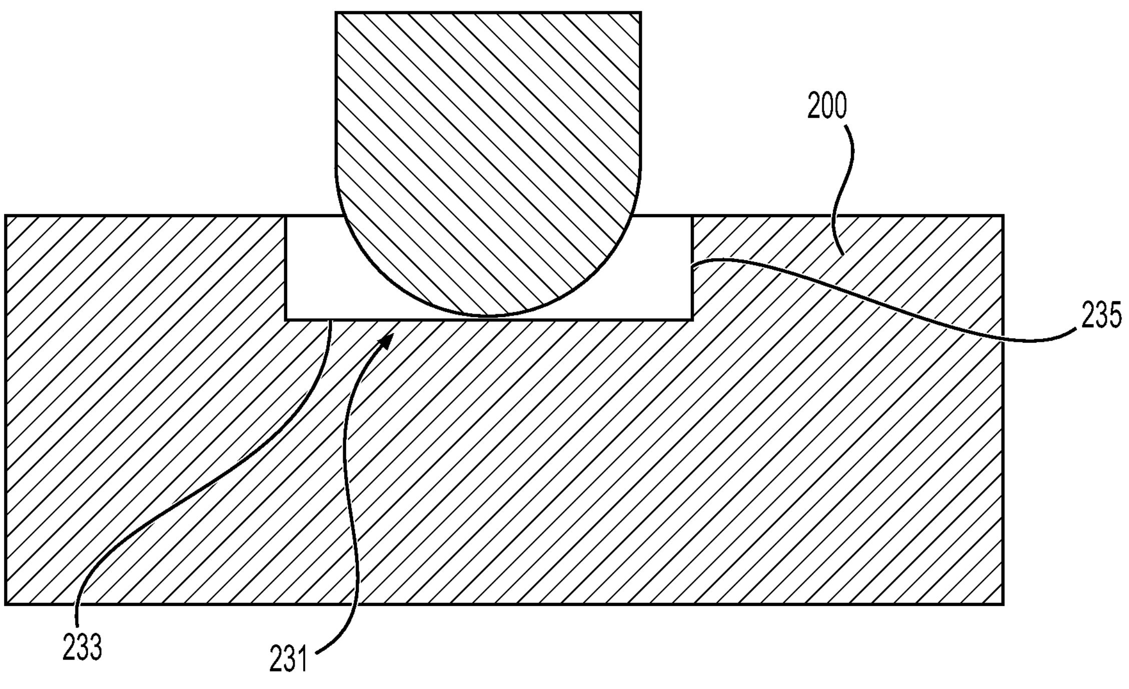
FIG. 8B is a side cross-sectional view of another embodiment of the third receiving component of the bone plate mating with a third coupling component of the guide block.
Figure 11:
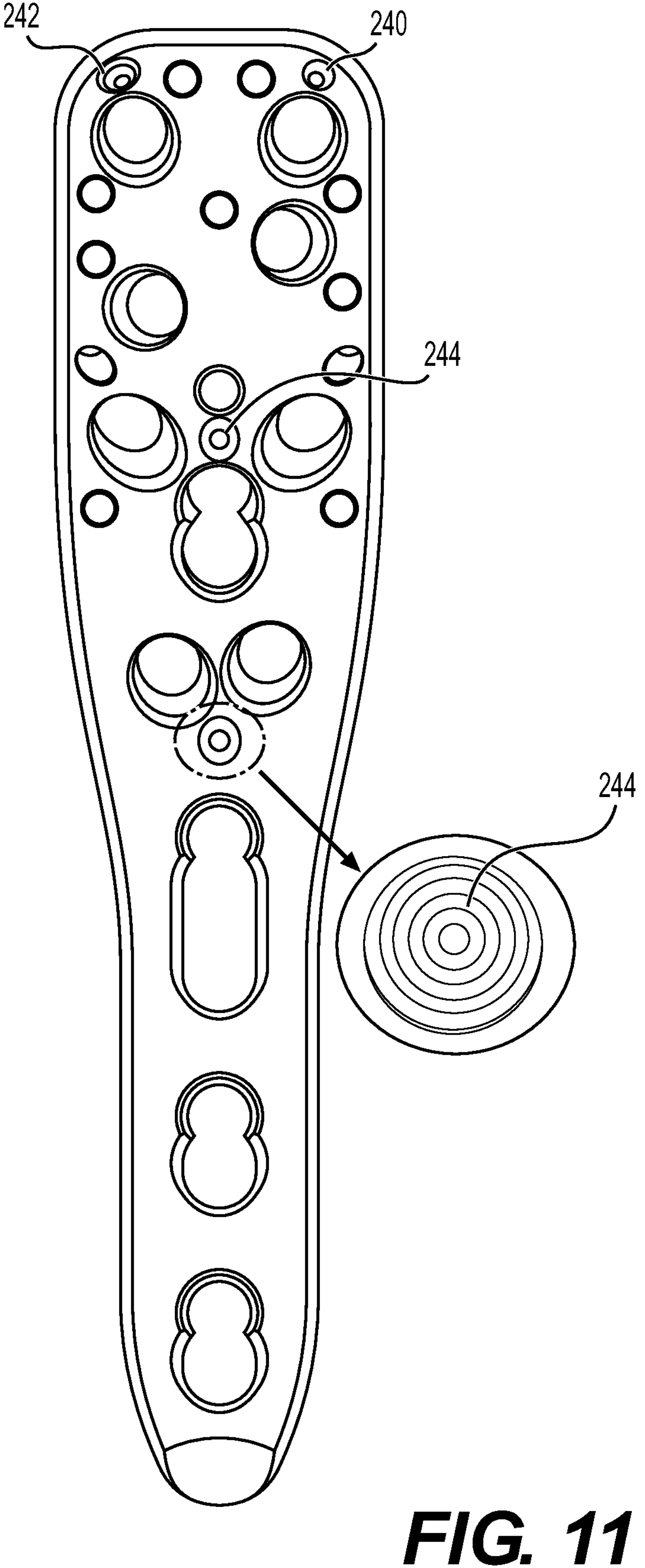
FIG. 11 is a top plan view of the bone plate showing concentric circles on the first, second and third receiving components of the bone plate.

Referring now to FIGS. 2A-2C, 5C, and 8A-8B, the third receiving component 230, 230' and the third coupling component 330, 330' mate with one another. Third coupling component 330, 330' has a hemispherical shaped projection. Third receiving component 230, 230' has a third recess 230A, 230A' that is shaped to receive the hemispherical shape of the third coupling component 330 such that, when mated, relative motion between the third receiving component 230 and the third coupling component 330 is restricted in a sixth degree of freedom. The sixth degree of freedom is non-overlapping with the first, second, third, fourth and fifth degrees of freedom. As shown in FIGS. 8A-8B, the bottom surface 230, 230' of third recess 230A, 230A' is in contact with the bottom surface of the third coupling component 330, 330', respectively. Thus, third coupling component 330, 330' contacts bottom surface 230, 230' at one location. More specifically, second coupling component 320, 320' contacts bottom surface 230, 230' of third recess 230A, 230A' at one point of contact on the bottom surface 230, 230' as shown in FIGS. 8A-8B.

Referring now to FIGS. 9A, 9B, 10 and 11, bone plate 200 and guide block 300, 300' are shown having a series of indicia in the form of concentric circles 240, 242, 244, 340, 340', 342, 342', 344, 344' formed on each of the first, second and third receiving components and on the first, second and third coupling components. The concentric circles can be, for example, etched onto the bone plate and guide block. The concentric circles could also be applied to the bone plate and guide block surfaces by other techniques, such as, for example, engraving, milling, carving, etc. The concentric circles 240, 242, 244, 340, 340', 342, 342', 344, 344' aid the user when mating bone plate 200 and guide block 300, 300' together. The user can readily identify that the first coupling component should mate with the first receiving component, the second coupling component should mate with the second receiving component, and the third coupling component should mate with the third receiving component.

To fully mate guide block 300, 300' to bone plate 200, the user will align the first coupling component with the first receiving component, the second coupling component with the second receiving component, and the third coupling component with the third receiving component. Once fully mated, the user can use a set screw 150 to fixedly connect the guide block 300 to bone plate 200. Set screw 150, shown in FIG. 1, is placed through opening 308, 308' in the guide block 300 and threaded into post bore 206 in bone plate 200. Guide block 300 can be repeatedly used in procedures with, of course, subjecting guide block 300 to a sterilization process, such as, for example, steam sterilization in an autoclave between each use. Other sterilization processed may be used, such as, for example, chemical, radiation or filtration processes as is known to those skilled in the art. Because guide block 300 is reused for multiple procedures, the location of the coupling components can be manufactured to higher tolerances than the location of the receiving components on the bone plate 200. In addition, because only the first coupling component with the first receiving component are a sphere-to-sphere mate the position of only the first coupling component on the guide block will determine the location of the bone plate 200 with respect to the guide block 300, 300'. The user will thus have a greater degree of certainty as to determining the position of the bone plate with respect to the guide block because only one point of contact between the guide block and the bone plate will determine the relative location of these two parts. The second coupling component of the guide block can mate anywhere within the ledges of the second receiving component of the bone plate. The third coupling component of the guide block can mate anywhere on the flat surface of the third receiving component of the bone plate.

The present disclosure is further illustrated by the following aspects of the disclosure.

1. A bone plate and guide block system (100) comprising:
   a bone plate (200) comprising a first receiving component (210), a second receiving component (220), and a third receiving component (230, 230'); and
   a guide block (300) comprising a first coupling component (310, 310'), a second coupling component (320, 320'), and a third coupling component (330, 330'),
   the first receiving component (210) and the first coupling component (310, 310') being adapted to mate with one another such that relative motion between the first receiving component (210) and the first coupling component (310, 310') is restricted in a first degree of freedom, a second degree of freedom, and a third degree of freedom,
   the second receiving component (220) and the second coupling component (320, 320') being adapted to mate with one another such that relative motion between the second receiving component (220) and the second coupling component (320, 320') is restricted in a fourth degree of freedom and a fifth degree of freedom, the fourth and fifth degrees of freedom being non-overlapping with the first, second, and third degrees of freedom, and
   the third receiving component (230) and the third coupling component (330, 330') being adapted to mate with one another such that relative motion between the third receiving component (230) and the third coupling component (330, 330') is restricted in a sixth degree of freedom, the sixth degree of freedom being non-overlapping with the first, second, third, fourth and fifth degrees of freedom.
2. The bone plate and guide block system (100) of clause 1, the first degree of freedom being a first translational degree of freedom, the second degree of freedom being a second translational degree of freedom, and the third degree of freedom being a third translational degree of freedom.
3. The bone plate and guide block system (100) of any one of clauses 1-2, the fourth degree of freedom being a first rotational degree of freedom, and the fifth degree of freedom being a second rotational degree of freedom.
4. The bone plate and guide block system (100) of any one of clauses 1-3, the sixth degree of freedom being a third rotational degree of freedom.
5. A bone plate (200) comprising a first receiving component (210), a second receiving component (220), and a third receiving component (230, 230') being configured to mate with respective coupling components (310, 320, 330, 330') of a guide block (300, 300') such that: (i) the first receiving component (210) restricts relative motion between the bone plate (200) and the guide block (300, 310') in a first degree of freedom, a second degree of freedom, and a third degree of freedom, (ii) the second receiving component (220) and the second coupling component (320, 320') restricts relative motion between the bone plate (200) and the guide block (300, 310') in a fourth degree of freedom and a fifth degree of freedom, the fourth and fifth degrees of freedom being non-overlapping with the first, second, and third degrees of freedom, and (iii) the third receiving component (230) and the third coupling component (330, 330') restricts relative motion between the bone plate (200) and the guide block (300, 310') in a sixth degree of freedom, the sixth degree of freedom being non-overlapping with the first, second, third, fourth and fifth degrees of freedom.

6. The bone plate (200) of clause 5, the first degree of freedom being a first translational degree of freedom, the second degree of freedom being a second translational degree of freedom, and the third degree of freedom being a third translational degree of freedom.

7. The bone plate (200) of any one of clauses 5-6, the fourth degree of freedom being a first rotational degree of freedom, and the fifth degree of freedom being a second rotational degree of freedom.

8. The bone plate (200) of any one of clauses 5-7, the sixth degree of freedom being a third rotational degree of freedom.

9. A coupling for connecting a first object (200) and a second object (300, 300'), the coupling comprising:
   - a first receiving component (210) associated with the first object (200), the first receiving component (210) defining a first recess (210A) that further defines a first receiving component semi-spherical surface (212);
   - a second receiving component (220) associated with the first object (200), the second receiving component (220) defining a second recess (220A) that further defines opposing ledges (222) proximal an upper end of the second recess (220A), the second recess (220A) being elongated in a length direction of the second recess (220A) relative to a width direction of the second recess (220A);
   - a third receiving component (230, 230') associated with the first object (200), the third receiving component (230) defining a third recess (230A) that further defines a third receiving component planar bottom surface (232);
   - a first coupling component (310, 310') associated with the second object (300, 300'), the first coupling component (310, 310') having a distal end that includes a first coupling component semi-spherical surface (314, 314');
   - a second coupling component (320, 320') associated with the second object (300, 300'), the second coupling component (320, 320') having a distal end that includes a second coupling component surface (324, 324'); and
   - a third coupling component (330, 330') associated with the second object (300, 300'), the third coupling component (330, 330') having a distal end that includes a third coupling semi-spherical surface (334, 334'),
   - the first receiving component (210) and the first coupling component (310, 310') being adapted to mate with one another along a first axis (64) such that the first coupling component semi-spherical surface (314, 314') is seated against the first receiving component semi-spherical surface (212),
   - the second receiving component (220) and the second coupling component (320, 320') being adapted to mate with one another along a second axis (66) such that the second coupling component surface (324, 324', 325) is seated against the opposing ledges (222),
   - the third receiving component (230) and the third coupling component (330, 330') being adapted to mate with one another along a third axis (68) such that the third coupling semi-spherical surface (334, 334') is seated against the third receiving component planar bottom surface (232), and
   - relative motion between (i) the first receiving component (210) and the first coupling component (310, 310'), when mated, (ii) the second receiving component (220) and the second coupling component (320, 320'), when mated, and (iii) the third receiving component (230) and the third coupling component (330, 330'), when mated, being restricted in all six degrees of freedom.

10. The coupling of clause 9, further comprising a second third receiving component (230') associated with the first object (200).

11. The coupling of any one of clauses 9-10, a radius of the first coupling component (310) and a radius of the first coupling component semi-spherical surface (212) being approximately equal.

12. The coupling of any one of clauses 9-11, a diameter of the second coupling component (320) being greater than a width of the second recess (220A).

13. The coupling of any one of clauses 9-12, the second coupling component surface (324, 324') being semi-spherically shaped.

14. The coupling of any one of clauses 9-12, the second coupling component surface (325) being conically shaped.

15. The coupling of any one of clauses 9-14, the opposing ledges (222) being defined by an upper edge of a sidewall (226) of the second recess (220A) and a lower edge of a chamfer (226) such that the opposing ledges (222) are disposed below an uppermost surface (202) of the first object (200).

16. The coupling of any one of clauses 9-15, a depth of the second recess (220A) being sized such that, when mated, the second coupling component (320, 320') does not contact a bottom surface (228, 228') of the second recess (220A).

17. The coupling of clause 16, the bottom surface (228, 228') of the second recess (220A) being inclined or oriented generally horizontally.

18. The coupling of any one of clauses 9-17, a diameter of the third recess (230A) being greater than a diameter of the third coupling component (330, 330').

19. The coupling of any one of clauses 9-18, a sidewall (234) of the third recess (230A) widening in diameter towards an upper end of the third recess (230A).

20. The coupling of any one of clauses 9-19, a sidewall (234) of the third recess (230A) having a constant diameter.

21. The coupling of any one of clauses 9-20, the first axis (64), the second axis (66), and the third axis (68) being generally orthogonal to a first object longitudinal axis (60, 60').

22. A bone plate (200) comprising:
   - a rigid plate body having:
     - an upper surface (202);
     - a lower surface (204)
     - at least one post bore (206);
     - a plurality of bone plate bores (208) defined therethrough, each bone plate bore comprising at least one angle of orientation;
     - a first recess (210A) formed in the upper surface (202) and defining a first semi-spherical surface (212);
     - a second recess (220A) formed in the upper surface (202) and defining opposing ledges (222) proximal an upper end of the second recess (220A), the second recess (220A) being elongated in a length direction of the second recess (220A) relative to a width direction of the second recess (220A); and a third recess (230A) formed in the upper surface (202) and defining planar bottom surface (232), the first semi-spherical surface (212), the opposing ledges (222), and the planar bottom surface (232) being configured to mate with respective protrusion surfaces (314, 324, 334) of a guide block (300, 300') such that relative motion between the rigid plate body and the guide block (300, 300') is restricted in all six degrees of freedom.

23. The bone plate (200) of clause 22, the first recess (210A) and the second recess (220A) being formed in the upper surface (202) proximal to a first lateral end of the rigid plate body, and the third recess (230A) being distal to the first lateral end of the rigid plate body.

24. The bone plate (200) of any one of clauses 22-23, the rigid plate body further having a fourth recess (230A') formed in the upper surface (202) and defining a planar bottom surface (232').

25. The bone plate (200) of any one of clauses 22-24, the opposing ledges (222) being defined by an upper edge of a sidewall (224) of the second recess (220A) and a lower edge of a chamfer (226) such that the opposing ledges (222) are disposed below the upper surface (202) of the rigid plate body.

26. The bone plate (200) of any one of clauses 22-25, a depth of the second recess (220A) being sized such that, when mated, the respective protrusion surface (324, 324', 325) of the guide block (300, 300') does not contact a bottom surface (228, 228') of the second recess (220A).

27. The bone plate (200) of clause 26, the bottom surface (228, 228') of the second recess (220A) being inclined or oriented generally horizontally.

28. The bone plate (200) of any one of clauses 22-27, a sidewall (234) of the third recess (230A) widening in diameter towards an upper end of the third recess (230A).

29. The bone plate (200) of any one of clauses 22-28, a sidewall (234) of the third recess (230A) having a constant diameter.

30. The bone plate (200) of any one of clauses 22-29, the first recess (210A) comprising a first indicia (240), the second recess (220A) comprising a second indicia (242), and the third recess comprising a third indicia (244).

31. The bone plate (200) of clause 30, the first indicia (240), the second indicia (242), and the third indicia (244) comprising etched circles.

32. A bone plate and guide block system (100) comprising:

a bone plate (200) comprising a rigid plate body having:

a first lateral end (200A);

a second lateral end (200B);

an upper surface (202);

a lower surface (204);

at least one post bore (206);

a plurality of plate bores (208) defined therethrough, each bone plate bore comprising at least one angle of orientation;

a first recess (210A) formed in the upper surface (202) and defining a first semi-spherical surface (212);

a second recess (220A) formed in the upper surface (202) and defining opposing ledges (222) proximal an upper end of the second recess (220A), the second recess (220A) being elongated in a length direction of the second recess (220A) relative to a width direction of the second recess (220A); and a third recess (230A) formed in the upper surface (202) and defining planar bottom surface (232); and a guide block (300) comprising:

a rigid guide block body (302);

a first coupling protrusion (310, 310') extending from the rigid guide block body (302), the first coupling protrusion (310, 310') having a distal end that includes a first coupling protrusion semi-spherical surface (314, 314');

a second coupling protrusion (320, 320') extending from the rigid guide block body (302), the second coupling protrusion (320, 320') having a distal end that includes a second coupling protrusion surface (324, 324', 325); and a third coupling protrusion (330, 330') extending from the rigid guide block body (302), the third coupling protrusion (330, 330') having a distal end that includes a third coupling protrusion semi-spherical surface (334, 334'), the first semi-spherical surface (212), the opposing ledges (222), and the planar bottom surface (232) mating with the first coupling protrusion semi-spherical surface (314), the second coupling protrusion surface (324, 324', 325), and the third coupling protrusion semi-spherical surface (334), respectively, such that relative motion between the bone plate (200) and the guide block (300, 300') is restricted in all six degrees of freedom.

33. The system (100) of clause 32, the bone plate (200) having a fourth recess (230A') formed in the upper surface (202) and defining a planar bottom surface (232'), the fourth recess (230A') being more proximal to the first lateral end than the third recess (230A).

34. The system (100) of any one of clauses 32-33, a radius of the first coupling protrusion (310) and a radius of the first semi-spherical surface (212) being approximately equal.

35. The system (100) of any one of clauses 32-34, a diameter of the second coupling protrusion (320) being greater than a width of the second recess (220A).

36. The system (100) of any one of clauses 32-35, the opposing ledges (222) being defined by an upper edge of a sidewall (226) of the second recess (220A) and a lower edge of a chamfer (226) such that the opposing ledges (222) are disposed below an uppermost surface (202) of the bone plate (200).

37. The system (100) of any one of clauses 32-36, a depth of the second recess (220A) being sized such that the second coupling protrusion (320, 320') is spaced from a bottom surface (228, 228') of the second recess (220A).

38. The system (100) of clause 37, the bottom surface (228, 228') of the second recess (220A) being inclined or oriented generally horizontally.

39. The system (100) of any one of clauses 32-38, the second coupling protrusion surface (324, 324') being semi-spherically shaped.

40. The system (100) of any one of clauses 32-39, the second coupling protrusion surface (325) being conically shaped.

41. The system (100) of any one of clauses 32-40, a diameter of the third recess (230A) being greater than a diameter of the third coupling protrusion (330, 330').
42. The system (100) of any one of clauses 32-41, a sidewall (234) of the third recess (230A) widening in diameter towards an upper end of the third recess (230A).
43. The system (100) of any one of clauses 32-42, a sidewall (234) of the third recess (230A) having a constant diameter.
44. The system (100) of any one of clauses 32-43, the bone plate (200) having a longitudinal axis (60), with the first lateral end and the second lateral end being oppositely disposed along the longitudinal axis (60), with the first recess (210A) and the second recess (220A) being formed in the upper surface (202) proximal to the first lateral end, and the third recess (230A) being distal to the first lateral end of the rigid plate body.
45. The system (100) of any one of clauses 32-44, the first recess (210A) comprising a first indicia (240), the second recess (220A) comprising a second indicia (242), and the third recess comprising a third indicia (244).
46. The system (100) of clause 45, the first indicia (240), the second indicia (242), and the third indicia (244) comprising etched circles.
47. The system (100) of any one of clauses 32-46, the rigid guide block body (302) comprising an upper surface (304), the upper surface (304) comprising a first indicia (340), a second indicia (342), and a third indicia (344).
48. The system (100) of clause 47, the first indicia (340) and the first coupling protrusion (310, 310') being generally aligned along a first axis (64), the second indicia (342) and the second coupling protrusion (320, 320') being generally aligned along a second axis (66), and the third indicia (344) and the third coupling protrusion (330, 330') being generally aligned along a third axis (68).
49. A bone plate (200) comprising:
    a rigid plate body having:
        an upper surface (202);
        a lower surface (204)
        at least one post bore (206);
        a plurality of plate bores (208) defined therethrough, each bone plate bore comprising at least one angle of orientation;
        a first recess (210A) formed in the upper surface (202) and defining a semi-spherical surface (212);
        a second recess (220A) formed in the upper surface (202) and defining a cylindrical sidewall (225) with a cylindrical upper ledge (223); and
        a third recess (230A) formed in the upper surface (202) and defining planar bottom surface (232),
        the semi-spherical surface (212), the cylindrical upper ledge (223), and the planar bottom surface (232) being configured to mate with respective protrusion surfaces (314, 324, 334) of a guide block (300, 300') such that relative motion between the rigid plate body and the guide block (300, 300') is restricted in all six degrees of freedom.

The descriptions contained herein are examples of embodiments of the invention and are not intended in any way to limit the scope of the invention. As described herein, the invention contemplates many variations and modifications of the guide block and bone plate, including, but not limited to, those described above. Modifications and variations apparent to those having skilled in the pertinent art according to the teachings of this disclosure are intended to be within the scope of the clauses which follow.

What is claimed is:

1. A bone plate and guide block system comprising:

a bone plate comprising a first receiving component, a second receiving component, and a third receiving component; and a guide block comprising a first coupling component, a second coupling component, and a third coupling component, the first receiving component and the first coupling component being adapted to mate with one another such that relative motion between the first receiving component and the first coupling component is restricted in a first degree of freedom, a second degree of freedom, and a third degree of freedom, the second receiving component and the second coupling component being adapted to mate with one another such that relative motion between the second receiving component and the second coupling component is restricted in a fourth degree of freedom and a fifth degree of freedom, the fourth and fifth degrees of freedom being non-overlapping with the first, second, and third degrees of freedom, the third receiving component and the third coupling component being adapted to mate with one another such that relative motion between the third receiving component and the third coupling component is restricted in a sixth degree of freedom, the sixth degree of freedom being non-overlapping with the first, second, third, fourth and fifth degrees of freedom, and relative motion between (i) the first receiving component and the first coupling component, when mated, (ii) the second receiving component and the second coupling component, when mated, and (iii) the third receiving component and the third coupling component when mated, is restricted in all six degrees of freedom.

2. The bone plate and guide block system of claim 1, wherein the first receiving component defines a first recess that further defines a first receiving component semi-spherical surface, the first coupling component has a distal end that comprises a first coupling component semi-spherical surface, the first receiving component and the first coupling component are adapted to mate with one another such that the first coupling component semi-spherical surface is seated against the first receiving component semi-spherical surface, and the first degree of freedom is a first translational degree of freedom, the second degree of freedom is a second translational degree of freedom, and the third degree of freedom is a third translational degree of freedom.

3. The bone plate and guide block system of claim 1, wherein the second receiving component defines a second recess that further defines opposing ledges proximal an upper end of the second recess, the second recess being elongated in a length direction of the second recess relative to a width direction of the second recess, the second coupling component has a distal end that comprises a second coupling component surface, the second receiving component and the second coupling component are adapted to mate with one another such that the second coupling component surface is seated against the opposing ledges, and the fourth degree of freedom is a first rotational degree of freedom, and the fifth degree of freedom is a second rotational degree of freedom.

4. The bone plate and guide block system of claim 1, wherein the third receiving component defines a third recess that further defines a third receiving component planar bottom surface, the third coupling component has a distal end that comprises a third coupling semi-spherical surface, the third receiving component and the third coupling component are adapted to mate with one another such that the third coupling semi-spherical surface is seated against the third receiving component planar bottom surface, and the sixth degree of freedom is a third rotational degree of freedom.

5. A bone plate comprising a first receiving component, a second receiving component and a third receiving component being configured to mate with respective first, second, and third coupling components of a guide block such that:

(i) the first receiving component and the first coupling component restricts relative motion between the bone plate and the guide block in a first degree of freedom, a second degree of freedom, and a third degree of freedom, (ii) the second receiving component and the second coupling component restricts relative motion between the bone plate and the guide block in a fourth degree of freedom and a fifth degree of freedom, the fourth and fifth degrees of freedom being non-overlapping with the first, second, and third degrees of freedom, (iii) the third receiving component and the third coupling component restricts relative motion between the bone plate and the guide block in a sixth degree of freedom, the sixth degree of freedom being non-overlapping with the first, second, third, fourth and fifth degrees of freedom, and (iv) relative motion between (a) the first receiving component and the first coupling component, when mated, (b) the second receiving component and the second coupling component, when mated, and (c) the third receiving component and the third coupling component when mated, is restricted in all six degrees of freedom.

6. The bone plate of claim 5, wherein the first receiving component defines a first recess that further defines a first receiving component semi-spherical surface, and the first degree of freedom is a first translational degree of freedom, the second degree of freedom is a second translational degree of freedom, and the third degree of freedom is a third translational degree of freedom.

7. The bone plate of claim 5, wherein the second receiving component defines a second recess that further defines opposing ledges proximal an upper end of the second recess, the second recess being elongated in a length direction of the second recess relative to a width direction of the second recess, and the fourth degree of freedom is a first rotational degree of freedom, and the fifth degree of freedom is a second rotational degree of freedom.

8. The bone plate of claim 5, wherein the third receiving component defines a third recess that further defines a third receiving component planar bottom surface, and the sixth degree of freedom is a third rotational degree of freedom.

9. A coupling for connecting a first object and a second object, the coupling comprising:

a first receiving component associated with the first object, the first receiving component defining a first recess that further defines a first receiving component semi-spherical surface;

a second receiving component associated with the first object, the second receiving component defining a second recess that further defines opposing ledges proximal an upper end of the second recess, the second recess being elongated in a length direction of the second recess relative to a width direction of the second recess;

a third receiving component associated with the first object, the third receiving component defining a third recess that further defines a third receiving component planar bottom surface;

a first coupling component associated with the second object, the first coupling component having a distal end that includes a first coupling component semi-spherical surface;

a second coupling component associated with the second object, the second coupling component having a distal end that includes a second coupling component surface; and a third coupling component associated with the second object, the third coupling component having a distal end that includes a third coupling semi-spherical surface, the first receiving component and the first coupling component being adapted to mate with one another along a first axis such that the first coupling component semi-spherical surface is seated against the first receiving component semi-spherical surface, the second receiving component and the second coupling component being adapted to mate with one another along a second axis such that the second coupling component surface is seated against the opposing ledges, the third receiving component and the third coupling component being adapted to mate with one another along a third axis such that the third coupling semi-spherical surface is seated against the third receiving component planar bottom surface, and relative motion between (i) the first receiving component and the first coupling component, when mated, (ii) the second receiving component and the second coupling component, when mated, and (iii) the third receiving component and the third coupling component when mated, being restricted in all six degrees of freedom.

10. The coupling of claim 9, further comprising a second third receiving component associated with the first object.

11. The coupling of claim 10, a radius of the first coupling component and a radius of the first coupling component semi-spherical surface being approximately equal.

12. The coupling of claim 11, a diameter of the second coupling component being greater than a width of the second recess.

13. The coupling of claim 12, the second coupling component surface being semi-spherically shaped.

14. The coupling of claim 12, the second coupling component surface being conically shaped.

15. The coupling of claim 9, the opposing ledges being defined by an upper edge of a sidewall of the second recess and a lower edge of a chamfer such that the opposing ledges are disposed below an uppermost surface of the first object.

16. The coupling of claim 15, a depth of the second recess being sized such that, when mated, the second coupling component does not contact a bottom surface of the second recess.

17. The coupling of claim 16, the bottom surface of the second recess being inclined or oriented generally horizontally.

18. The coupling of claim 9, a diameter of the third recess being greater than a diameter of the third coupling component.

19. The coupling of claim 18, a sidewall of the third recess widening in diameter towards an upper end of the third recess.

20. The coupling of claim 19, a sidewall of the third recess having a constant diameter.

* * * * *